(12) United States Patent
Garcia Molina

(10) Patent No.: US 11,207,022 B2
(45) Date of Patent: Dec. 28, 2021

(54) SYSTEM AND METHOD FOR DETERMINING SLEEP STAGES BASED ON CARDIAC ACTIVITY INFORMATION AND BRAIN ACTIVITY INFORMATION IN EEG SIGNALS

(71) Applicant: KONINKLIJKE PHILIPS N.V., Eindhoven (NL)

(72) Inventor: Gary Nelson Garcia Molina, Madison, WI (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 360 days.

(21) Appl. No.: 16/062,180

(22) PCT Filed: Dec. 20, 2016

(86) PCT No.: PCT/EP2016/081891
§ 371 (c)(1),
(2) Date: Jun. 14, 2018

(87) PCT Pub. No.: WO2017/108766
PCT Pub. Date: Jun. 29, 2017

(65) Prior Publication Data
US 2018/0360376 A1 Dec. 20, 2018

Related U.S. Application Data

(60) Provisional application No. 62/270,890, filed on Dec. 22, 2015.

(51) Int. Cl.
*A61B 5/00* (2006.01)
*A61B 5/291* (2021.01)
(Continued)

(52) U.S. Cl.
CPC ............ *A61B 5/4812* (2013.01); *A61B 5/291* (2021.01); *A61B 5/369* (2021.01); *A61B 5/4809* (2013.01);
(Continued)

(58) Field of Classification Search
CPC . A61B 5/02405; A61B 5/0476; A61B 5/0478; A61B 5/4809; A61B 5/4812;
(Continued)

(56) References Cited

U.S. PATENT DOCUMENTS 6,272,378 B1  8/2001  Baumgart-Schmitt
7,578,793 B2 *  8/2009  Todros ................. A61B 5/0402
                                         600/300

(Continued)

FOREIGN PATENT DOCUMENTS

CN   103584840 A   2/2014
CN   104970773 A   10/2015
(Continued)

OTHER PUBLICATIONS

Lambert, Empirical Mode Decomposition, Rice University, https://www.clear.rice.edu/elec301/Projects02/empiricalMode/(Year: 2015).*
(Continued)

*Primary Examiner* — Jonathan T Kuo

(57) ABSTRACT

The present disclosure pertains to a system configured to determine sleep stages in a subject based on cardiac artifact information and brain activity information in EEG signals. Cardiac artifacts present in EEG signals can cause erroneous sleep stage determinations which may result in inopportune sensory stimulation during sleep, no stimulation at all, discarding long periods of EEG signal information, and/or other events. The present system enhances real-time sleep stage determinations compared to prior art systems and/or provides other advantages because the present system deter-
(Continued)

mines the current sleep stage of the subject based on both cardiac activity information and brain activity information included in the EEG signals.

18 Claims, 7 Drawing Sheets

(51) Int. Cl.
    *A61B 5/369*         (2021.01)
    *A61B 5/024*         (2006.01)

(52) U.S. Cl.
    CPC ............ *A61B 5/7203* (2013.01); *A61B 5/725* (2013.01); *A61B 5/7278* (2013.01); *A61B 5/02405* (2013.01); *A61B 5/7207* (2013.01); *A61B 5/7246* (2013.01)

(58) Field of Classification Search
    CPC ... A61B 5/7203; A61B 5/7207; A61B 5/7246; A61B 5/725; A61B 5/7278
    See application file for complete search history.

(56) References Cited

U.S. PATENT DOCUMENTS

| | | | | |
|---|---|---|---|---|
| 8,948,861 | B2* | 2/2015 | Rai | ...................... A61B 5/4806 340/540 |
| 2006/0111635 | A1* | 5/2006 | Todros | ................. A61B 5/0402 600/484 |
| 2012/0253220 | A1* | 10/2012 | Rai | ...................... A61B 5/0476 600/544 |
| 2014/0114165 | A1 | 4/2014 | Walker et al. | |

FOREIGN PATENT DOCUMENTS

| | | | |
|---|---|---|---|
| EP | 2526858 | A1 | 11/2012 |
| JP | 2011083474 | A | 4/2011 |
| JP | 2011110378 | A * | 6/2011 |
| WO | 2014068537 | A2 | 5/2014 |
| WO | 2014167457 | A1 | 10/2014 |

OTHER PUBLICATIONS

2011 Google English Translation of JP 2011110378 (Year: 2011).*
Abdullah, H. et al., "Correlation of sleep EEG frequency bands and heart rate variability", Proceedings of the 31st Annual International Conference of the IEEE Engineering in Medicine and Biology Society: Engineering the Future of Biomedicine, EMBC 2009, IEEE, Sep. 3, 2009.
Jiang et al., "An automatic analysis method for detecting and eliminating ECG artifacts in EEG", Computers in Biology and Medicine, vol. 37, No. 11, Sep. 6, 2007.
S. Devuyst, T. Dutoit, P. Stenuit, M. Kerkhofs, and E. Stanus, "Cancelling ECG artifacts in EEG using a modified independent component analysis approach," EURASIP J. Adv. Signal Process., vol. 2008, p. 13 pages, 2008.
F. Chouchou and M. Desseilles, "Heart rate variability: a tool to explore the sleeping brain?," Auton. Neurosci., vol. 8, no. December, pp. 1-9, 2014.
S. Devuyst, T. Dutoit, P. Stenuit, M. Kerkhofs, and E. Stanus, "Removal of ECG artifacts from EEG using a modified independent component analysis approach.," in Annual International Conference of the IEEE Engineering in Medicine and Biology Society, 2008, vol. 2008, No. 1, pp. 5204-5207.
J. F. Kaiser, "Some useful properties of Teager's energy operators," in IEEE International Conference on Acoustics Speech and Signal Processing, 1993, vol. 3, pp. 149-152.
M. E. Huang, Z. Shen, S. R. Long, M. C. Wu, H. H. Shih, Q. Zheng, N.-C. Yen, C. C. Tung, and H. H. Liu, "The empirical mode decomposition and the Hilbert spectrum for nonlinear and non-stationary time series analysis," Proc. R. Soc. A Math. Phys. Eng. Sci., vol. 454, No. 1971, pp. 903-995, Mar. 1998.
S. Elsenbruch, M. J. Hamish, and W. C. Orr, "Heart rate variability during waking and sleep in healthy males and females.," Sleep, vol. 22, No. 8, pp. 1067-1071, 1999.

* cited by examiner

SYSTEM AND METHOD FOR DETERMINING SLEEP STAGES BASED ON CARDIAC ACTIVITY INFORMATION AND BRAIN ACTIVITY INFORMATION IN EEG SIGNALS

Cross-Reference to Prior Applications

This application is the U.S. National Phase application under 35 U.S.C. §371 of International Application Serial No. PCT/EP2016/081891, filed on 20 Dec. 2016, which claims the benefit of U.S. Application Ser. No. 62/270890, filed on 22 Dec. 2015. These applications are hereby incorporated by reference herein.

BACKGROUND

1. Field

The present disclosure pertains to a system and method for determining sleep stages based on cardiac artifact information and brain activity information in electroencephalography (EEG) signals.

2. Description of the Related Art

Systems for monitoring sleep are known. Determining sleep stages during sleep is known. Typically, sleep stages are determined based on information from an EEG. The presence of cardiac artifacts in a sleep EEG disrupts sleep stage determinations and often results in erroneous deep sleep and/or wake determinations.

SUMMARY

Accordingly, one or more aspects of the present disclosure relate to a system configured to determine sleep stages of a subject during a sleep session. The system comprises one or more sensors, one or more hardware processors, and/or other components. The one or more sensors are configured to generate output signals conveying information related to brain activity of the subject. The output signals include cardiac artifact information related to cardiac activity of the subject with the information related to brain activity. The one or more hardware processors operatively communicate with the one or more sensors. The one or more hardware processors are configured, by machine-readable instructions, to demodulate the output signals to separate the information related to brain activity and the cardiac artifact information; determine one or more brain activity parameters based on the separated information related to brain activity; determine one or more cardiac activity parameters based on the separated cardiac artifact information; and determine the sleep stages of the subject during the sleep session based on the one or more brain activity parameters and the one or more cardiac activity parameters.

Yet another aspect of the present disclosure relates to a method for determining sleep stages of a subject during a sleep session with a determination system. The system comprises one or more sensors, one or more hardware processors, and/or other components. The method comprises generating, with the one or more sensors, output signals conveying information related to brain activity of the subject, the output signals including cardiac artifact information related to cardiac activity of the subject with the information related to brain activity; demodulating, with the one or more hardware processors, the output signals to separate the information related to brain activity and the cardiac artifact information; determining, with the one or more hardware processors, one or more brain activity parameters based on the separated information related to brain activity; determining, with the one or more hardware processors, one or more cardiac activity parameters based on the separated cardiac artifact information; and determining, with the one or more hardware processors, the sleep stages of the subject during the sleep session based on the one or more brain activity parameters and the one or more cardiac activity parameters.

Still another aspect of present disclosure relates to a system configured to determine sleep stages of a subject during a sleep session. The system comprises means for generating output signals conveying information related to brain activity of the subject, the output signals including cardiac artifact information related to cardiac activity of the subject with the information related to brain activity; means for demodulating the output signals to separate the information related to brain activity and the cardiac artifact information; means for determining one or more brain activity parameters based on the separated information related to brain activity; means for determining one or more cardiac activity parameters based on the separated cardiac artifact information; and means for determining the sleep stages of the subject during the sleep session based on the one or more brain activity parameters and the one or more cardiac activity parameters.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
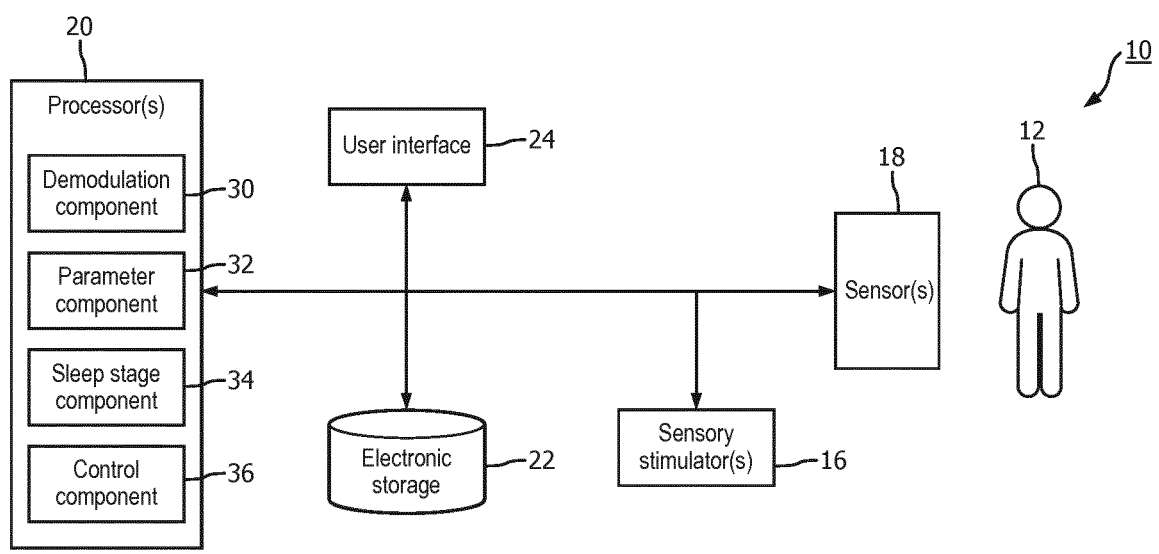
FIG. 1 is a schematic illustration of a system configured to determine sleep stages in a subject based on cardiac artifact information and brain activity information in EEG output signals.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a schematic illustration of a system 10 configured to determine sleep stages in a subject 12 based on cardiac artifact information and brain activity information in electroencephalography (EEG) signals. Cardiac artifacts present in EEG signals can cause erroneous sleep stage determinations which may result in inopportune sensory stimulation during sleep (e.g., stimulation that is not timed with deep sleep), no stimulation at all, discarding long periods of EEG signal information, and/or other events. System 10 enhances real-time sleep stage determinations compared to prior art systems and/or provides other advantages. System 10 determines the current sleep stage of subject 12 based on both cardiac artifact information and brain activity information included in the EEG signals. System 10 takes advantage of cardiac activity that interferes with EEG signals by separating the brain activity information from the cardiac artifact information in the EEG signals using a demodulation algorithm, and independently processing the brain activity information and the cardiac artifact information. Processing the cardiac artifact information enables, among other things, the enhanced detection of rapid eye movement (REM) sleep via an estimation of heart rate variability (HRV) and/or other cardiac parameters.

Cardiac activity artifacts manifest in an EEG because the cardiac electric field affects the surface potentials on the scalp of subject 12. Cardiac artifacts in EEG signals recorded during sleep may cause errors during automatic interpretation of sleep recordings (e.g., sleep stage determinations). The presence of cardiac artifacts in the form of spikes in the EEG signal may cause artificial increases in power in one or more power bands of the EEG (discussed below). For example, spikes in the beta band (about 15-30 Hz) may occur. Since activity in the beta band is usually indicative of micro-arousals, an EEG segment containing such spikes may be erroneously scored (e.g., by an automatic algorithm) as a wakeful period even though subject 12 is sleeping deeply. When cardiac artifacts manifest in the EEG in the form of regular pulses, the regular pulses may be incorrectly detected as slow-waves (discussed below). Pulse artifacts may appear when a reference EEG electrode is placed near major arteries, for example. This may result in periods of light sleep being confounded as periods of deep sleep and therefore causing unwanted sensory stimulation during light sleep. Because of these and/or other issues that arise during the automatic analysis of EEG signals contaminated with cardiac artifacts, the usual strategy to handle portions of the EEG with cardiac artifacts comprises discarding these portions. This can lead to substantially long portions of an EEG being discarded.

System 10 is configured to utilize the cardiac artifact information present in the EEG to improve automatic sleep stage determinations instead of rejecting and/or discarding the portions of the EEG containing cardiac artifacts. Determining sleep stages based on cardiac artifact information improves the accuracy of sleep stage determination because changes in cardiac parameters of subject 12 (e.g., heart rate variability (HRV)) reveal the presence of REM sleep (discussed below) and/or other sleep stages. One or more features of system 10 may be especially advantageous in single electrode EEG systems because it is challenging to reliably detect REM sleep with a single EEG electrode based on brain activity information alone.

Figure 2:
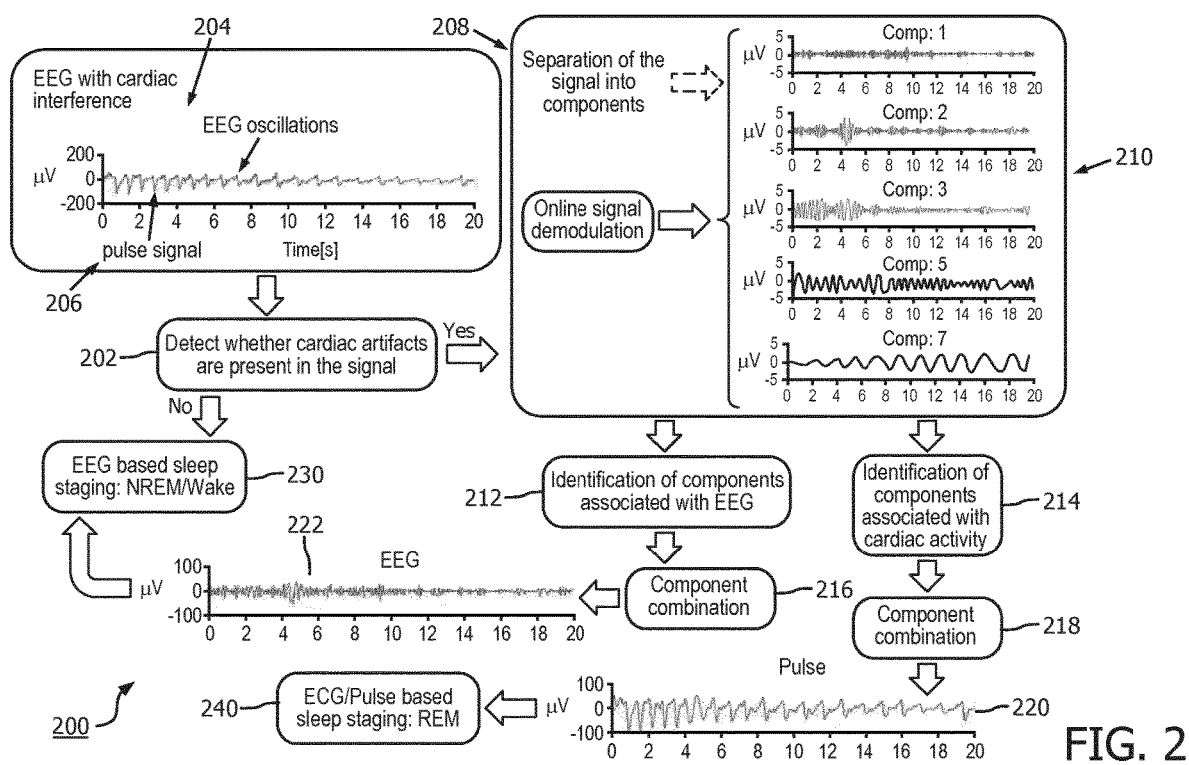
FIG. 2 summarizes basic operations performed by the system.

FIG. 2 summarizes basic operations 200 performed by system 10 (shown in FIG. 1). Operation 202 comprises determining whether or not the acquired EEG signal 204 includes cardiac artifacts 206. If the signal includes cardiac artifacts 206 as illustrated in FIG. 2, then a demodulation operation 208 takes place wherein brain activity information and cardiac artifact information in the EEG signal are separated from each other. The demodulation process produces several signal components 210 whose summation reconstructs the original EEG signal. The components with information that contributes to the brain activity information in the EEG and the components with information that contributes to the cardiac artifact information are identified by their spectral properties 212, 214. The components with information that contributes to the brain activity information are then additively combined 216 to reconstruct the brain activity portion of the EEG signal 222. Similarly, the components with information that contributes to the cardiac artifact information are additively combined 218 to reconstruct a cardiac signal 220. The reconstructed brain activity signal 222 is used to determine 230 non-rapid eye movement (NREM) sleep stages. The reconstructed cardiac signal 220 is processed to extract heart rate variability (HRV) and/or other cardiac parameters and then identify 240 REM sleep. The paragraphs below elaborate on this summary.

Returning to FIG. 1, in some embodiments, system 10 comprises one or more of a sensory stimulator, a sensor 18, a processor 20, electronic storage 22, a user interface 24, and/or other components. In FIG. 1, sensory stimulator 16, sensor 18, processor 20, electronic storage 22, and user interface 24 are shown as separate entities. This is not intended to be limiting. Some and/or all of the components of system 10 and/or other components may be grouped into one or more singular devices. For example, some and/or all of the components of system 10 may be grouped as part of a headband and/or other garments worn by subject 12.

Sensory stimulator 16 is configured to provide sensory stimuli to subject 12. Sensory stimulator 16 is configured to provide sensory stimulation to subject 12 prior to a sleep session, during a current sleep session, after a sleep session, and/or at other times. For example, sensory stimulator 16 may be configured to provide sensory stimuli to subject 12 during slow wave sleep (described below) in a sleep session. Sensory stimulator 16 may be configured to provide sensory stimulation to subject 12 during a sleep session to induce, maintain, and/or adjust slow wave activity (SWA, EEG power in the 0.5 to 4 Hz band) in subject 12. In some embodiments, sensory stimulator 16 may be configured such that adjusting includes increasing, decreasing, and/or other adjustment of SWA in subject 12. In some embodiments, the delivery of the sensory stimulation is timed to correspond to sleep stages associated with SWA, is timed to wake subject 12 from sleep, and/or timed to correspond to other sleep in subject 12.

In some embodiments, sensory stimulator 16 may be configured to induce and/or adjust SWA through non-invasive brain stimulation and/or other methods. Sensory stimulator 16 may be configured to induce and/or adjust SWA through non-invasive brain stimulation using sensory stimuli. The sensory stimuli include odors, sounds, visual stimulation, touches, tastes, and/or other stimuli. For example, transcranial magnetic stimulation may be applied to subject 12 to trigger, increase, and/or decrease SWA. As another example, sensory stimulator 16 may be configured to induce and/or adjust SWA via auditory stimulation of subject 12. Examples of sensory stimulator 16 may include one or more of a music player, a tone generator, a collection of electrodes on the scalp of subject 12, a unit to deliver vibratory stimulation (also known as somato-sensory stimulation), a coil generating a magnetic field to directly stimulate the brain's cortex, light generators, a fragrance dispenser, and/or other devices.

Sensor 18 is configured to generate output signals conveying information related to brain activity of subject 12 and/or other information. Sensor 18 is configured to generate output signals in an ongoing manner during the sleep session of subject 12, at regular intervals during the sleep session, and/or at other times. The output signals include cardiac artifact information related to cardiac activity of the subject with the information related to brain activity. The brain activity of subject 12 may correspond to a current sleep stage, SWA in subject 12, and/or other characteristics of subject 12. The brain activity of subject 12 may be associated with rapid eye movement (REM) sleep, non rapid eye movement (NREM) sleep, and/or other sleep. Sleep stages of subject 12 may include one or more of NREM stage N1, stage N2, or stage N3 sleep, REM sleep, and/or other sleep stages. In some embodiments, N1 corresponds to a light sleep state and N3 corresponds to a deep sleep state. In some embodiments, NREM stage 3 or stage 2 sleep may be slow wave (e.g., deep) sleep. Sensor 18 may comprise one or more sensors that measure such parameters directly and/or indirectly. For example, sensor 18 may include electrodes configured to detect electrical activity along the scalp of subject 12 resulting from current flows within the brain of subject 12. In some embodiments, one or more sensors 18 are EEG electrodes, and/or other sensors. An EEG exhibits changes throughout a sleep session. A prominent change in the EEG delta power (also known as slow wave activity (SWA)) is typically visible, for example. SWA corresponds to the power of an EEG signal in the 0.5-4.5 Hz band. In some embodiments, this band is set to 0.5-4 Hz. SWA has a typical behavior throughout cyclic variations of a given sleep session. SWA increases during non-rapid eye movement sleep (NREM), declines before the onset of rapid-eye-movement (REM) sleep, and remains low during REM. SWA in successive NREM episodes progressively decreases from one episode to the next. SWA may be estimated, and/or slow wave sleep (e.g., stage N3) may be determined from an EEG for subject 12 during a given sleep session.

Although sensor 18 is illustrated at a single location near subject 12, this is not intended to be limiting. Sensor 18 may include sensors disposed in a plurality of locations, such as for example, coupled in a removable manner with the skin of subject 12, coupled in a removable manner with clothing of subject 12, worn by subject 12 (e.g., as a headband, wristband, etc.), and/or in other locations. For example, sensor 18 may be removably coupled with the skin of subject 12 via a sticker and/or other coupling mechanisms such that cardiac artifacts are induced on purpose. In these embodiments, sensor 18 is placed slightly below the mastoid of subject 12 near major arteries of subject 12.

Processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some embodiments, processor 20 may comprise a plurality of processing units. These processing units may be physically located within the same device (e.g., sensor 18), or processor 20 may represent processing functionality of a plurality of devices operating in coordination.

As shown in FIG. 1, processor 20 is configured to execute one or more computer program components. The one or more computer program components may comprise one or more of a demodulation component 30, a parameter component 32, a sleep stage component 34, a control component 36, and/or other components. Processor 20 may be configured to execute components 30, 32, 34, 36 and/or other components by software; hardware; firmware; some combination of software, hardware, and/or firmware; and/or other mechanisms for configuring processing capabilities on processor 20.

It should be appreciated that although components 30, 32, 34, and 36 are illustrated in FIG. 1 as being co-located within a single processing unit, in embodiments in which processor 20 comprises multiple processing units, one or more of components 30, 32, 34, 36, and/or other components may be located remotely from the other components. The description of the functionality provided by the different components 30, 32, 34, 36, and/or other components described below is for illustrative purposes, and is not intended to be limiting, as any of components 30, 32, 34, and/or 36 may provide more or less functionality than is described. For example, one or more of components 30, 32, 34, and/or 36 may be eliminated, and some or all of its functionality may be provided by other components 30, 32, 34, and/or 36. As another example, processor 20 may be configured to execute one or more additional components that may perform some or all of the functionality attributed below to one of components 30, 32, 34, and/or 36.

Demodulation component 30 is configured to demodulate the output signals (e.g., an EEG signal) from sensor 18 (e.g., EEG electrodes). The output signals are demodulated to separate the information related to brain activity and the cardiac artifact information. In some embodiments, demodulation component 30 is configured to determine whether cardiac artifact information is present before commencing demodulation. In some embodiments, demodulating the output signals and/or determining whether cardiac artifact information is present may include generating and/or monitoring an EEG during a sleep session of subject 12. The EEG may be displayed, for example, by user interface 24. Given an EEG signal and/or other signals from sensor 18, an EEG itself (e.g., displayed by user interface 24), and/or other information, the presence of cardiac artifacts in the signal is detected based on the occurrence of periodic spikes in the signal and a lack of correlation of the spikes with the background EEG. An equation for a signal containing the cardiac artifact "y(n)" can then be written as:

$$y(n) = x(n) + s(n) \tag{1}$$

where x(n) is the EEG related portion of the signal and s(n) is the cardiac artifact which may comprise, for example, regularly spaced spikes in the signal. The Teager-Kaiser energy operator "$\Psi[\bullet]$" (see Equation 2) can be used to detect uncorrelated spike activity, for example.

$$\Psi[y(n)] = y^2(n) - y(n+1) \cdot y(n-1) \tag{2}$$

Since x(n) and s(n) are uncorrelated, Equation 3 holds:

$$\Psi[y(n)] = \Psi[x(n)] + \Psi[s(n)] \tag{3}$$

In addition, for spiking activity, $\Psi[y(n)] \approx \Psi[s(n)]$, and for non-spiking activity $\Psi[s(n)] \approx 0$. Thus, $\Psi[y(n)]$ has maximum values when spikes are present in the signal. Demodulation component 30 is configured to set thresholds on $\Psi[y(n)]$ amplitude (e.g., at least 200 $\mu V^2$) and spike duration (e.g. up to about 40 milliseconds between amplitude threshold crossings) and detect cardiac spikes (artifacts) in the signal when one or both of these thresholds are breached. Once the candidate cardiac spikes are detected, the next step comprises estimating statistics on the inter-spike interval. The median inter-spike interval is particularly useful, for example, because if this median is in the interval between about 0.8 and about 1.5 s, then it is likely that a cardiac artifact is present in the signal.

Figure 3:
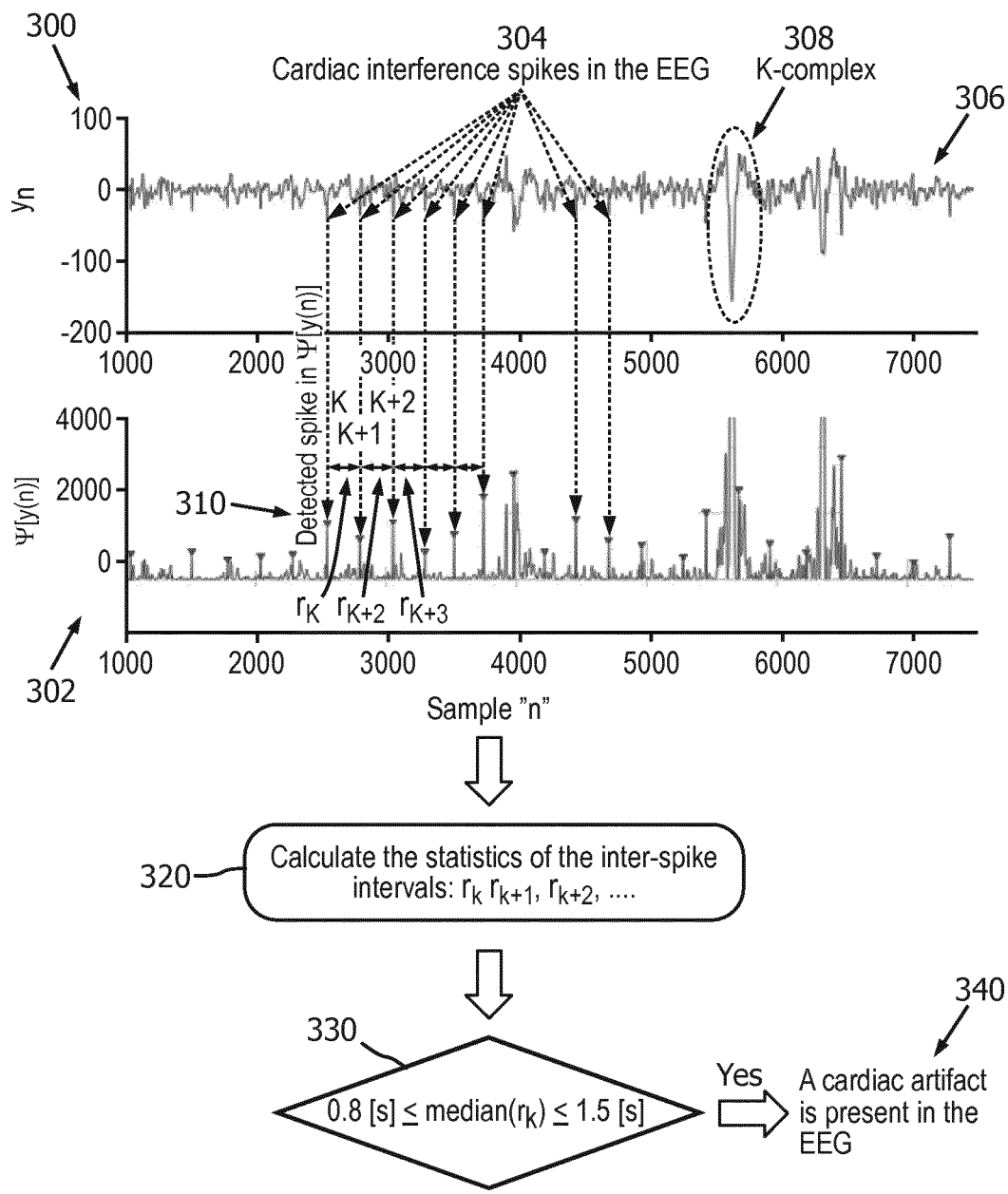
FIG. 3 illustrates detection of cardiac artifacts in the EEG output signals.

By way of a non-limiting example, FIG. 3 illustrates detection of cardiac artifacts in output (e.g., EEG) signals from sensors 18 (FIG. 1). Two signals 300, 302 are illustrated in FIG. 3. Signal 300 illustrates the presence of cardiac spikes 304 in an EEG 306. EEG 306 indicates subject 12 (FIG. 1) is in sleep stage N2 given the presence of the K-complex 308. In FIG. 3, EEG 206 is sampled at 250 Hz (but this is not intended to be limiting). Signal 302 illustrates $\Psi[y(n)]$. The amplitude and duration thresholds are applied (e.g., as described above) by demodulation component 30 to identify 310 cardiac spikes 304. In FIG. 3, the duration of the interval between consecutive detected peaks "k" and "k+1" is referred to as $r_k$. Demodulation component 30 may then estimate 320 the median of, and/or other values and/or statistics related to, the $r_k$ intervals. If the median, for example, is between about 0.8 and about 1.5 seconds as indicated at reference numeral 330, demodulation component 30 determines 340 that the output (e.g., EEG) signals have cardiac artifacts. The time interval described above between about 0.8 and about 1.5 seconds is not intended to be limiting. Demodulation component 30 may be configured to detect cardiac artifacts based on any interval that allows system 10 to function as described herein. In some embodiments, the threshold levels described herein (e.g., amplitude thresholds, inter-peak interval thresholds, etc.) are determined at manufacture, determined by a user via user interface 24 (FIG. 1), automatically determined by processor 20 (FIG. 1), and/or determined by other methods.

Figure 4:
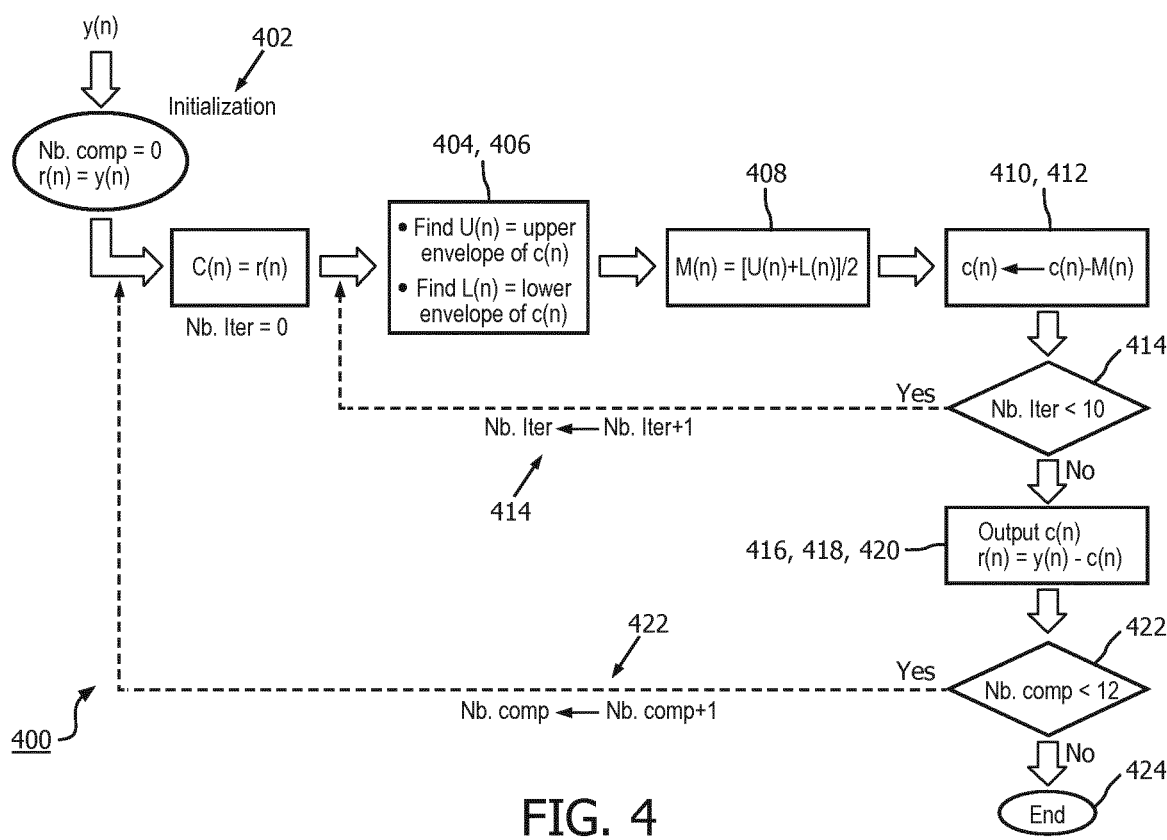
FIG. 4 illustrates an example of a demodulation decomposition process algorithm.

Returning to FIG. 1, in some embodiments, demodulation component 30 is configured such that demodulation (e.g., responsive to determining that cardiac artifacts are present in the sensor output signals) includes using an empirical mode decomposition framework to separate the output (e.g., EEG) signals from sensors 18 into one or more individual oscillatory components (e.g., intrinsic mode functions) related to brain activity and one or more individual oscillatory components (e.g., intrinsic mode functions) related to cardiac activity. An example of a decomposition process algorithm 400 is shown in FIG. 4. Demodulation component 30 (FIG. 1) is configured such that the decomposition process is iterative and comprises one or more of the following steps: initializing 402 the algorithm by setting a so-called residual signal r(n)=y(n), and both the number of iterations and the number of components to zero; identifying 404 local maxima and minima of an intrinsic mode function, c(n), and generating 406 the upper envelope U(n) and the lower envelope L(n) using spline interpolation, for example, on the local maxima and local minima respectively; determining 408 an average of the two envelopes M(n) =[U(n)+L(n)]/2; subtracting 410 M(n) from c(n) to obtain a component candidate, and assigning 412 this value to c(n) (e.g., c(n) ←c(n)−M(n)). In some embodiments, the upper envelope is the signal that is composed of the local maxima in pre-defined sliding windows of a given duration (e.g., 1 second with 0.5 second overlap). The lower envelope is the signal that is composed of the local minima in pre-defined sliding windows of a given duration (e.g., 1 second with 0.5 second overlap). In some embodiments, demodulation component 30 is configured to repeat 414 the steps after initialization 402 until the number of iterations is 10, for example. Ten iterations are used in this example but this is not intended to be limiting. Demodulation component 30 may use any number of iterations that identifies separate and stable individual oscillatory components as described above. In some embodiments, the number of iterations is determined at manufacture, determined by a user via user interface 24 (FIG. 1), automatically determined by processor 20 (FIG. 1), and/or determined by other methods.

After 10 iterations, for example, are complete, demodulation component 30 is configured to select 416 the resulting c(n) as an intrinsic mode function, determine 418 the difference r(n)=y(n)−c(n), and reassign 420 c(n) to r(n). Demodulation component 30 is configured to repeat 422 the process described above until the number of intrinsic mode functions reaches a predetermined quantity (e.g., 12), and then terminate 424 the process. In some embodiments, the predetermined quantity of intrinsic mode functions is determined at manufacture, determined by a user via user interface 24 (FIG. 1), automatically determined by processor 20 (FIG. 1), and/or determined by other methods.

Figure 5:
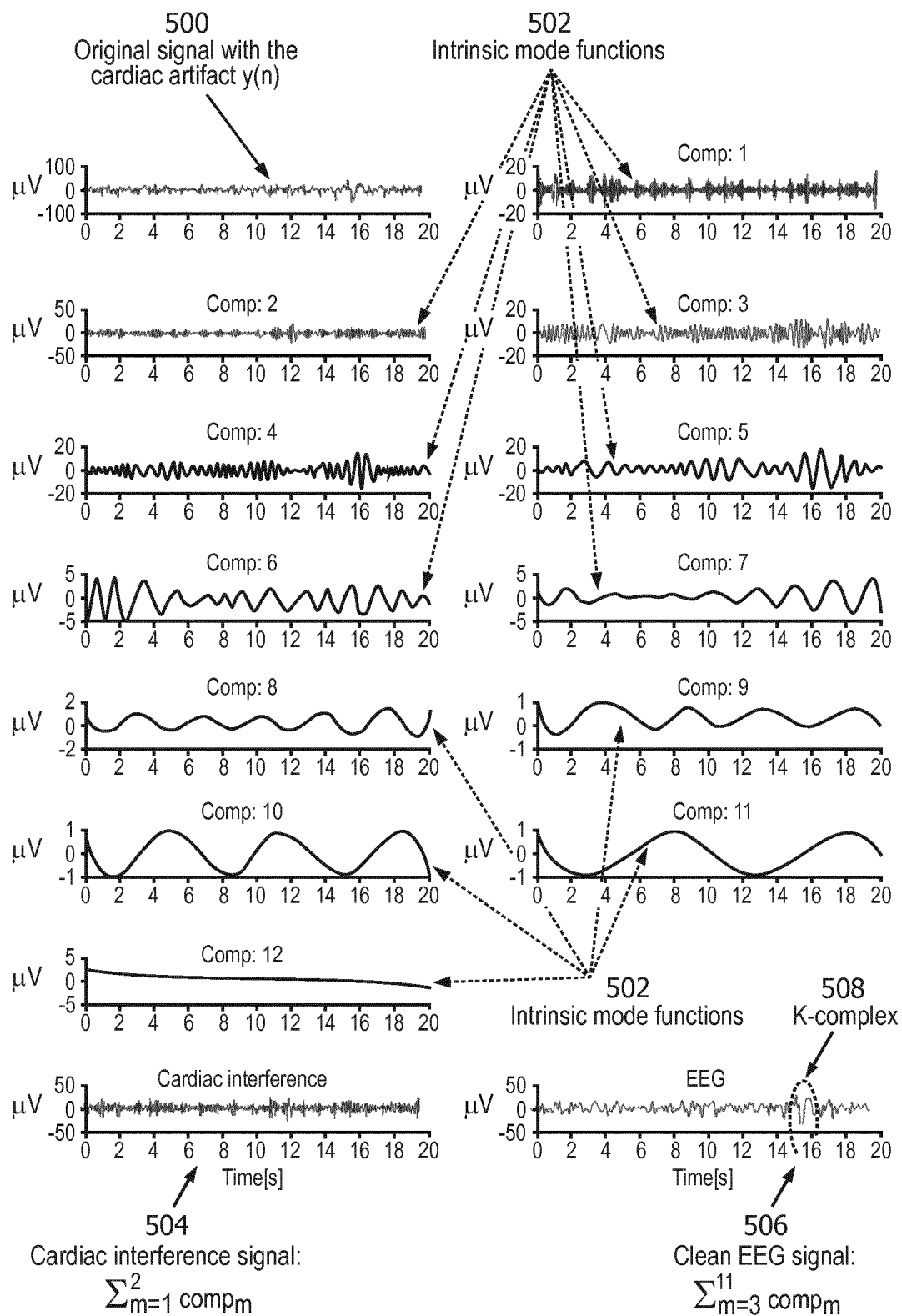
FIG. 5 illustrates separated individual oscillatory components resulting from the application of the demodulation decomposition process algorithm to the output signals.

FIG. 5 illustrates an output signal 500 y(n) from sensor 18 (FIG. 1) and separated individual oscillatory components 502 (e.g., intrinsic mode functions) resulting from the application of the decomposition algorithm to the output signal as described above. Out of 12 (for example) components 502 (intrinsic mode functions) identified via the algorithm, one or more may include (primarily) cardiac artifact information while one or more other components may include (primarily) brain activity (e.g., EEG) information. In some embodiments, demodulation component 30 determines whether an individual component includes primarily cardiac artifact information or primarily brain activity information based presence or lack of cardiac spikes (detected as described above) in the individual component. In the example shown in FIG. 5, Comp. 1 and Comp. 2 include primarily cardiac artifact information and Comp. 3—Comp. 11 include primarily brain activity information. Comp. 12 does not demonstrate cyclic behavior.

In some embodiments, demodulation component 30 is configured to additively combine components which include primarily cardiac artifact information (e.g., Comp. 1 and 2) to determine a cardiac interference signal 504. In some embodiments, demodulation component 30 is configured to additively combine the components which include primarily brain activity information (e.g., Comp. 3—Comp. 11) to determine a clean EEG signal 506. As shown in FIG. 5, EEG signal 506 displays a K-complex 508.

Figure 6:
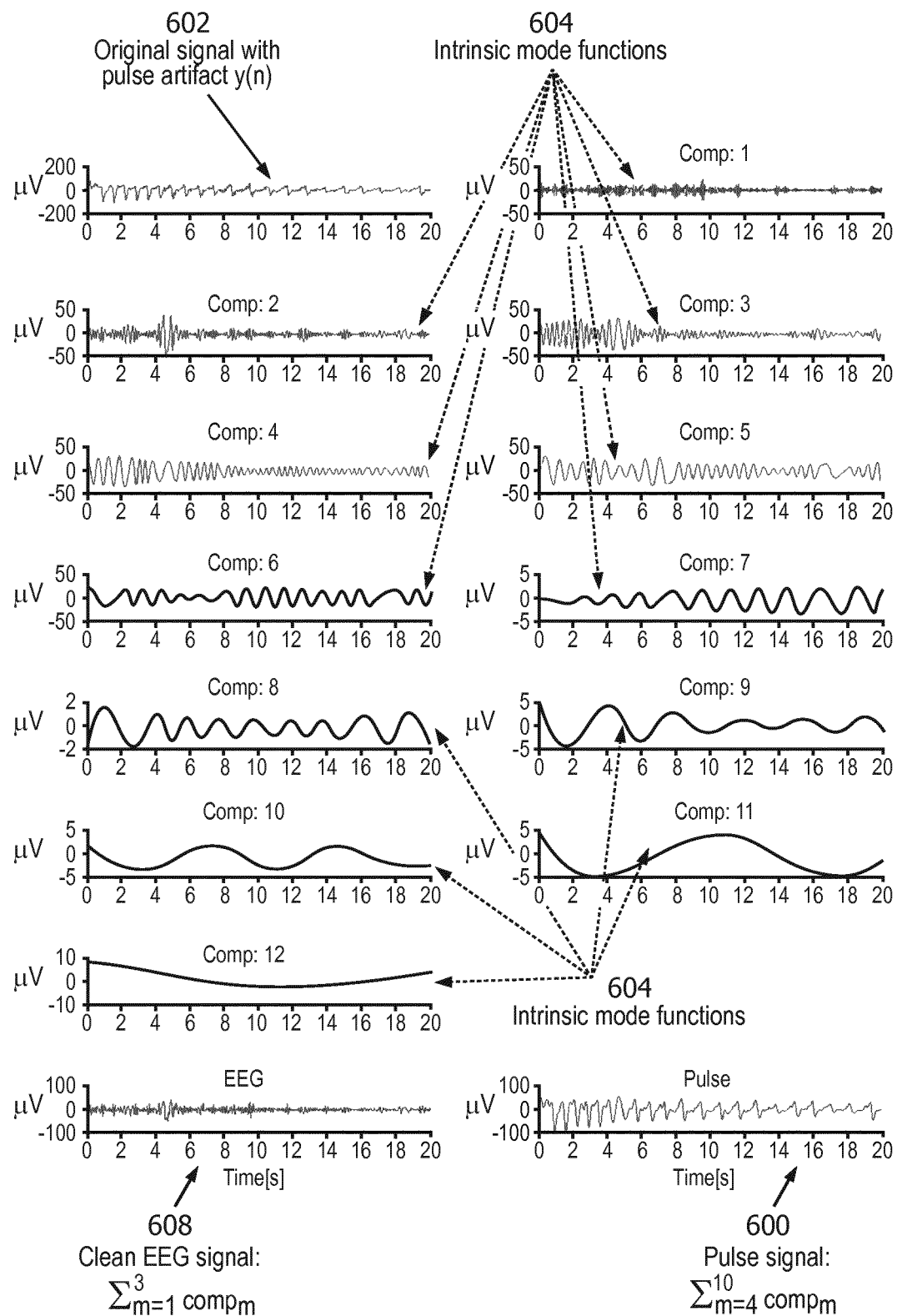
FIG. 6 illustrates cardiac interference that manifests as a pulse signal.

In some embodiments, cardiac interference manifests as a pulse signal 600 shown in FIG. 6. In the example shown in FIG. 6, original signal 602 has been separated into individual components (intrinsic mode functions 604) by demodulation component 30 (FIG. 1) as described above. Comp. 1—Comp. 3 are additively combined to determine pulse signal 600, and Comp. 4—Comp. 10 are additively combined to determine clean EEG signal 608. For this particular example, EEG signal 608 exhibits alpha oscillations (characteristic of a wake state with eyes closed).

Returning to FIG. 1, parameter component 32 is configured to determine one or more brain activity parameters, one or more cardiac activity parameters, and/or other parameters. In some embodiments, the one or more brain activity parameters are determined based on the separated information related to brain activity which may include a reconstructed EEG signal (e.g., EEG signal 506 shown in FIG. 5), and/or other information. In some embodiments, the one or more brain activity parameters include EEG related parameters such as power in various frequency bands of the EEG, ratios of power in a low frequency band to power in a high frequency band, and/or other parameters. In some embodiments, parameter component 32 is configured such that the one or more brain activity parameters are and/or are related to a frequency, amplitude, phase, presence of specific sleep patterns such as spindles, K-complexes, or sleep slow waves, alpha waves, and/or other characteristics of the EEG signal. In some embodiments, determining the one or more brain activity parameters includes additively combining and/or performing other mathematical operations on the individual oscillatory components related to brain activity. For example, in some embodiments, the one or more brain activity parameters are determined based on the frequency, amplitude, and/or other characteristics of the EEG signal. In some embodiments, the determined brain activity parameters and/or the characteristics of the EEG may be and/or indicate sleep states that correspond to the REM and/or NREM sleep stages described above. In some embodiments, the determined brain activity parameters are the REM and/or NREM sleep stages described above.

Figure 7:
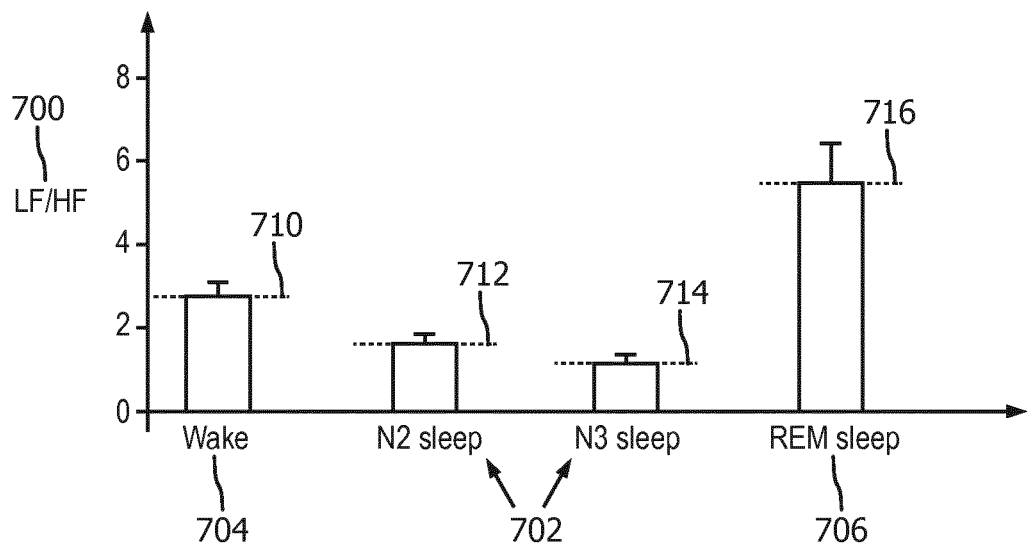
FIG. 7 illustrates low frequency to high frequency ratios (of spectral heartrate variability) for NREM sleep stages, wakefulness, and REM.

In some embodiments, the cardiac activity parameters are determined based on the separated cardiac artifact information and/or other information. The separated cardiac artifact information may include a reconstructed cardiac interference signal (e.g., cardiac interference signal 504) and/or other information. In some embodiments, the cardiac activity parameters include heart rate variability (HRV) and/or other cardiac activity parameters. In some embodiments, determining the one or more cardiac parameters includes additively combining and/or performing other mathematical operations on the individual oscillatory components related to cardiac activity. For example, parameter component 32 may determine an inter spike interval in a cardiac interference signal (e.g., signal 504 shown in FIG. 5). Parameter component 32 may determine HRV based on the inter spike interval and/or other information. The spikes are used to estimate the sequence of inter-spike intervals r1, r2, . . . , rQ as shown in FIG. 3 (element 320). These are used to estimate the spectral heart rate variability as the ratio between the power in the low frequency (LF) band (about 0.05 to about 0.15 Hz) and the power in the high frequency (HF) band (about 0.15 to about 0.4 Hz). The ratio LF/HF for REM (FIG. 7 element 706) is significantly higher than that for NREM sleep (FIG. 7 elements 702) or wakefulness (FIG. 7 element 704).

Sleep stage component 34 is configured to determine one or more sleep stages in subject 12. In some embodiments, sleep stage component 34 determines sleep stages in real-time or near real-time during a sleep session of subject 12. The sleep stages are determined based on the one or more brain activity parameters, the one or more cardiac activity parameters, and/or other information. In some embodiments, determining the sleep stages of subject 12 during the sleep session includes determining NREM sleep stages based on the one or more brain activity parameters, determining REM sleep stages based on the one or more brain activity parameters and the one or more cardiac activity parameters, and/or other determinations.

For example, in some embodiments, sleep stage component 34 is configured to determine sleep stages based on the ratio between the power in the low frequency band and the power in the high frequency band of the spectral heart rate variability. FIG. 7 illustrates low frequency to high frequency ratios (LF/HF) 700 for NREM sleep stages 702, wakefulness 704, and REM 706 for signal 300 shown in FIG. 3 (an example output signal from sensors 18). In some embodiments, sleep stage component 34 (FIG. 1) is configured to determine sleep stages based on breaches of threshold low frequency to high frequency ratio values for the individual sleep stages 710, 712, 714, 716. In some embodiments, sleep stage component 34 is configured to differentiate only REM from the other sleep stages based on a REM threshold ratio value 716. It should be noted that threshold values 710-716 are illustrated at the top of their respective graphical bars but this is not intended to be limiting. Threshold values 710-716 may have any values that allow system 10 (FIG. 1) to function as described herein. For example, threshold 716 for REM may be located at a ratio of about 3, so that REM sleep is detected as the LF/HF ratio increases beyond ratios indicative of wakefulness.

In some embodiments, sleep stage component 34 (FIG. 1) is configured to determine sleep stages based on EEG characteristics (e.g., parameters determined by parameter component 32) during NREM sleep including a transition from alpha waves (e.g., about 8-12 Hz) to theta waves (e.g., about 4-7 Hz) for sleep stage N1; presence of sleep spindles (e.g., about 11 to 16 Hz) and/or K-complexes (e.g., similar to sleep slow waves) for sleep stage N2; presence of delta waves (e.g., about 0.5 to 2 Hz), also known as sleep slow waves, with peak-to-peak amplitudes greater than about 75 microvolts for sleep stage N3; and/or other characteristics. The determined sleep stages may be sleep states such as light REM sleep, deep NREM sleep, and/or other sleep stages. Light NREM sleep may be a sleep state characterized by the fact that the alpha activity (e.g., EEG power in the 8-12 Hz band) is no longer present and slow wave activity is not yet present. In addition, spindle activity (EEG power in the 11 to 16 Hz band) may be high. Deep NREM sleep may be characterized by the fact that delta activity (e.g., EEG power in the 0 to 4 Hz band) is dominant, for example.

Returning to FIG. 1, control component 36 is configured to control sensory stimulator 16 to provide sensory stimulation to subject 12 during the sleep session and/or at other times. Control component 36 is configured to control sensory stimulator 16 based on the sleep stage information from sleep stage component 34, the parameter information from parameter component 32, the output signals from sensor 18, information determined during demodulation, and/or other information. Controlling sensory stimulator 16 includes determining a timing, a frequency, an intensity, and/or other parameters of the stimulation provided to subject 12. The timing, frequency, intensity, and/or other parameters of the stimulation provided to subject 12 may be controlled to increase and/or decrease slow wave activity, for example, in subject 12 during the sleep session, facilitate transitions between sleep states and/or stages, and/or for other reasons. The timing, frequency, intensity, and/or other parameter determinations may be determined based on information from previous sleep sessions of subject 12, sleep sessions of a representative group of subjects related to subject 12, may be determined at manufacture, and/or determined by other methods.

In some embodiments, control component 36 is configured to control sensory stimulator 16 such that the timing of the sensory stimuli (e.g., auditory tones) comprises a regular, repeating interval of time between individual stimuli delivered to subject 12 during stage N3 sleep and/or other sleep stages. In some embodiments, control component 36 may control sensory stimulator 16 to provide the sensory stimulation during the sleep session such that the sensory stimulation does not unintentionally wake subject 12.

Electronic storage 22 comprises electronic storage media that electronically stores information. The electronic storage media of electronic storage 22 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 22 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 22 may store software algorithms, algorithm inputs, information determined by processor 20, information received via user interface 24 and/or external computing systems, and/or other information that enables system 10 to function properly. Electronic storage 22 may be (in whole or in part) a separate component within system 10, or electronic storage 22 may be provided (in whole or in part) integrally with one or more other components of system 10 (e.g., processor 20).

User interface 24 is configured to provide an interface between system 10 and subject 12, and/or other users through which subject 12 and/or other users may provide information to and receive information from system 10. For example, user interface 24 may display an EEG to a user. This enables data, cues, results, instructions, and/or any other communicable items, collectively referred to as "information," to be communicated between a user (e.g., subject 12, a caregiver, and/or other users) and one or more of sensory stimulator 16, sensor 18, processor 20, electronic storage 22, and/or other components of system 10.

Examples of interface devices suitable for inclusion in user interface 24 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, user interface 24 comprises a plurality of separate interfaces. In some embodiments, user interface 24 comprises at least one interface that is provided integrally with processor 20, electronic storage 22, and/or other components of system 10.

It is to be understood that other communication techniques, either hard-wired or wireless, are also contemplated by the present disclosure as user interface 24. For example, the present disclosure contemplates that user interface 24 may be integrated with a removable storage interface provided by electronic storage 22. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 24 comprise, but are not limited to, an RS-232 port, RF link, an IR link, modem (telephone, cable or other). In short, any technique for communicating information with system 10 is contemplated by the present disclosure as user interface 24.

Figure 8:
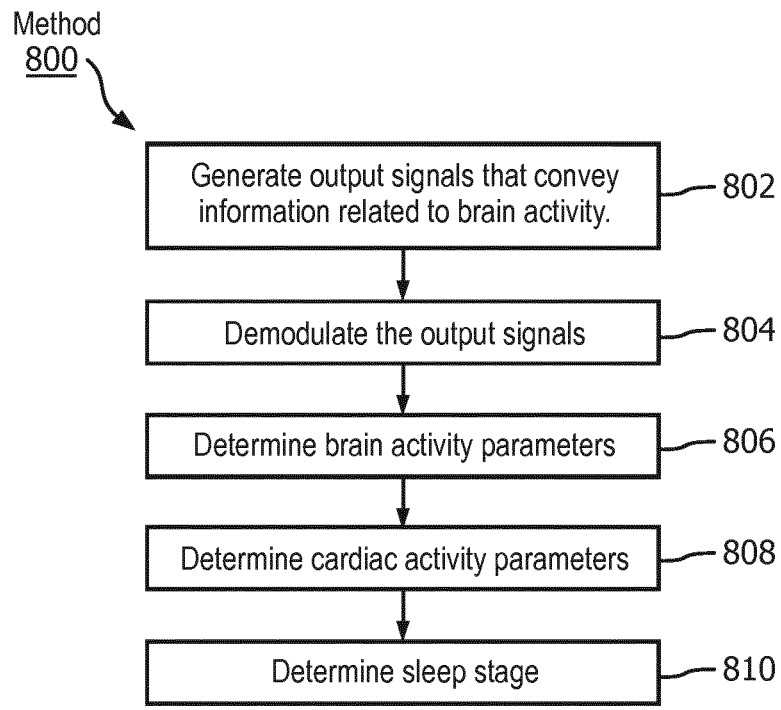
FIG. 8 illustrates a method for determining sleep stages based on cardiac artifact information in an EEG signal.

FIG. 8 illustrates a method 800 for determining sleep stages based on cardiac artifact information in an EEG signal with a determination system. The system comprises one or more sensors, one or more hardware processors, and/or other components. The operations of method 800 presented below are intended to be illustrative. In some embodiments, method 800 may be accomplished with one or more additional operations not described, and/or without one or more of the operations discussed. Additionally, the order in which the operations of method 800 are illustrated in FIG. 8 and described below is not intended to be limiting.

In some embodiments, method 800 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 800 in response to instructions stored electronically on an electronic storage medium. The one or more processing devices may include one or more devices configured through hardware, firmware, and/or software to be specifically designed for execution of one or more of the operations of method 800.

At an operation 802, output signals conveying information related to brain activity of the subject during a sleep session are generated. The output signals include cardiac artifact information related to cardiac activity of the subject with the information related to brain activity. In some embodiments, the one or more sensors are electroencephalogram (EEG) sensors, and/or other sensors. In some embodiments, operation 802 is performed by one or more sensors the same as or similar to sensors 18 (shown in FIG. 1 and described herein).

At an operation 804, the output signals are demodulated. The output signals are demodulated to separate the information related to brain activity and the cardiac artifact information. In some embodiments, operation 804 may include determining whether cardiac artifact information is present before demodulation commences and/or demodulation may include first determining whether cardiac artifact information is present. In some embodiments, demodulation includes using an empirical mode decomposition framework to separate the output signals into one or more individual oscillatory components related to brain activity and one or more individual oscillatory components related to cardiac activity. In some embodiments, operation 804 is performed by a hardware processor component the same as or similar to demodulation component 30 (shown in FIG. 1 and described herein).

At an operation 806, one or more brain activity parameters are determined based on the separated information related to brain activity. In some embodiments, the one or more brain activity parameters include EEG related parameters and/or other parameters. In some embodiments, determining the one or more brain activity parameters includes additively combining the individual oscillatory components related to brain activity. In some embodiments, operation 806 is performed by a hardware processor component the same as or similar to parameter component 32 (shown in FIG. 1 and described herein).

At an operation 808, one or more cardiac activity parameters are determined. The cardiac activity parameters are determined based on the separated cardiac artifact information. In some embodiments, the cardiac activity parameters include heart rate variability (HRV) and/or other cardiac activity parameters. In some embodiments, determining the one or more cardiac parameters includes additively combining the individual oscillatory components related to cardiac activity. In some embodiments, operation 808 is performed by a hardware processor component the same as or similar to parameter component 32 (shown in FIG. 1 and described herein).

At an operation 810, one or more sleep stages in the subject are determined. The sleep stages are determined based on the one or more brain activity parameters and the one or more cardiac activity parameters. In some embodiments, determining the sleep stages of the subject during the sleep session includes determining NREM sleep stages based on the one or more brain activity parameters and determining REM sleep stages based on the one or more brain activity parameters and the one or more cardiac activity parameters. In some embodiments, operation 810 is performed by a hardware processor component the same as or similar to sleep stage component 34 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to determine sleep stages of a subject during a sleep session, the system comprising:
   one or more sensors configured to generate output signals conveying information related to brain activity of the subject, the output signals including cardiac artifact information related to cardiac activity of the subject with the information related to brain activity; and
   one or more hardware processors operatively communicating with the one or more sensors configured, by machine-readable instructions, to:
   demodulate the output signals to separate the information related to brain activity and the cardiac artifact information;
   determine one or more brain activity parameters based on the separated information related to brain activity;
   determine one or more cardiac activity parameters based on the separated cardiac artifact information; and
   determine the sleep stages of the subject during the sleep session based on the one or more brain activity parameters and the one or more cardiac activity parameters,
   wherein the determining the sleep stages of the subject during the sleep session includes determining NREM sleep stages based on the one or more brain activity parameters and determining REM sleep stages based on the one or more brain activity parameters and the one or more cardiac activity parameters.

2. The system of claim 1, wherein the one or more sensors are electroencephalogram (EEG) sensors, and wherein the one or more hardware processors are configured such that the one or more brain activity parameters include one or more EEG parameters and the one or more cardiac activity parameters include heart rate variability and spectral heart rate variability.

3. The system of claim 1, wherein the one or more hardware processors are configured such that demodulation includes using an empirical mode decomposition framework to separate the output signals into one or more individual oscillatory components related to brain activity and one or more individual oscillatory components related to cardiac activity.

4. The system of claim 3, wherein the one or more hardware processors are configured such that determining the one or more brain activity parameters includes additively combining the individual oscillatory components related to brain activity and determining the one or more cardiac parameters includes additively combining the individual oscillatory components related to cardiac activity.

5. The system of claim 1, further comprising one or more sensory stimulators configured to provide sensory stimuli to the subject to induce, maintain, and/or adjust slow wave activity in the subject during the sleep session, the one or more sensory stimulators controlled by the one or more hardware processors based on the sleep stages of the subject determined based on the one or more brain activity parameters and the one or more cardiac activity parameters.

6. The system of claim 1, wherein the one or more hardware processor are further configured to determine whether cardiac artifacts are present in the output signals, and, responsive to a determination that cardiac artifacts are present in the output signals, proceed with demodulating the output signals to separate the information related to brain activity and the cardiac artifact information.

7. The system of claim 1, further comprising means for providing sensory stimuli to the subject to induce, maintain, and/or adjust slow wave activity in the subject during the sleep session, the means for providing sensory stimuli controlled based on the sleep stages of the subject determined based on the one or more brain activity parameters and the one or more cardiac activity parameters.

8. A method for determining sleep stages of a subject during a sleep session with a determination system, the system comprising one or more sensors and one or more hardware processors, the method comprising:
   generating, with the one or more sensors, output signals conveying information related to brain activity of the subject, the output signals including cardiac artifact information related to cardiac activity of the subject with the information related to brain activity;

demodulating, with the one or more hardware processors, the output signals to separate the information related to brain activity and the cardiac artifact information;

determining, with the one or more hardware processors, one or more brain activity parameters based on the separated information related to brain activity;

determining, with the one or more hardware processors, one or more cardiac activity parameters based on the separated cardiac artifact information; and determining, with the one or more hardware processors, the sleep stages of the subject during the sleep session based on the one or more brain activity parameters and the one or more cardiac activity parameters, wherein determining the sleep stages of the subject during the sleep session includes determining NREM sleep stages based on the one or more brain activity parameters and determining REM sleep stages based on the one or more brain activity parameters and the one or more cardiac activity parameters.

9. The method of claim 8, wherein the one or more sensors are electroencephalogram (EEG) sensors, the one or more brain activity parameters include one or more EEG parameters, and the one or more cardiac activity parameters include heart rate variability and spectral heart rate variability.

10. The method of claim 8, wherein demodulation includes using an empirical mode decomposition framework to separate the output signals into one or more individual oscillatory components related to brain activity and one or more individual oscillatory components related to cardiac activity.

11. The method of claim 10, wherein determining the one or more brain activity parameters includes additively combining the individual oscillatory components related to brain activity and determining the one or more cardiac parameters includes additively combining the individual oscillatory components related to cardiac activity.

12. The method of claim 8, further comprising providing, with one or more sensory stimulators included in the system, sensory stimuli to the subject to induce, maintain, and/or adjust slow wave activity in the subject during the sleep session, the one or more sensory stimulators controlled by the one or more hardware processors based on the sleep stages of the subject determined based on the one or more brain activity parameters and the one or more cardiac activity parameters.

13. The method of claim 8, further comprising determining, with the one or more hardware processors, whether cardiac artifacts are present in the output signals, and, responsive to a determination that cardiac artifacts are present in the output signals, proceed with demodulating the output signals to separate the information related to brain activity and the cardiac artifact information.

14. The method of claim 8, further comprising means for determining whether cardiac artifacts are present in the output signals, and, responsive to a determination that cardiac artifacts are present in the output signals, proceeding with demodulating the output signals to separate the information related to brain activity and the cardiac artifact information.

15. A system configured to determine sleep stages of a subject during a sleep session, the system comprising:

means for generating output signals conveying information related to brain activity of the subject, the output signals including cardiac artifact information related to cardiac activity of the subject with the information related to brain activity;

means for demodulating the output signals to separate the information related to brain activity and the cardiac artifact information;

means for determining one or more brain activity parameters based on the separated information related to brain activity;

means for determining one or more cardiac activity parameters based on the separated cardiac artifact information; and means for determining the sleep stages of the subject during the sleep session based on the one or more brain activity parameters and the one or more cardiac activity parameters, wherein determining the sleep stages of the subject during the sleep session includes determining NREM sleep stages based on the one or more brain activity parameters and determining REM sleep stages based on the one or more brain activity parameters and the one or more cardiac activity parameters.

16. The system of claim 15, wherein the means for generating output signals conveying information related to brain activity of the subject comprise electroencephalogram (EEG) sensors, the one or more brain activity parameters include one or more EEG parameters, and the one or more cardiac activity parameters include heart rate variability and spectral heart rate variability.

17. The system of claim 15, wherein demodulation includes using an empirical mode decomposition framework to separate the output signals into one or more individual oscillatory components related to brain activity and one or more individual oscillatory components related to cardiac activity.

18. The system of claim 17, wherein determining the one or more brain activity parameters includes additively combining the individual oscillatory components related to brain activity and determining the one or more cardiac parameters includes additively combining the individual oscillatory components related to cardiac activity.

* * * * *